United States Patent [19]
Thorn

[11] Patent Number: 5,938,026
[45] Date of Patent: Aug. 17, 1999

[54] SWAB DISPENSER

[75] Inventor: Mark Edward Thorn, River Vale, N.J.

[73] Assignee: Chesebrough-Pond's USA Co., Greenwich, Conn.

[21] Appl. No.: 09/033,199

[22] Filed: Mar. 2, 1998

[51] Int. Cl.[6] .................................................. B65D 83/10
[52] U.S. Cl. ...................... 206/362; 206/362.4; 220/833; 312/293.2
[58] Field of Search .................................. 206/361, 362, 206/362.4, 362.1, 370, 256, 259, 264, 268, 273, 229; 132/293, 318, 317; 220/833, 834, 835, 837, 23.83; 229/164.2, 120.35, 160.1; 312/293.2, 293.1, 231, 232, 327, 328, 310

[56] References Cited

U.S. PATENT DOCUMENTS

| | | | |
|---|---|---|---|
| 227,179 | 5/1880 | Robbins | 312/293.2 |
| 1,705,829 | 3/1929 | Stanley | 206/259 |
| 1,949,165 | 2/1934 | Krieger | 206/268 |
| 2,361,597 | 10/1944 | Buttery | 229/87.03 |
| 3,261,501 | 7/1966 | Capucio . | |
| 4,085,841 | 4/1978 | Matsuyama | 206/45.15 |
| 4,850,482 | 7/1989 | Campbell | 206/273 |
| 4,989,730 | 2/1991 | Lemoine . | |
| 5,147,035 | 9/1992 | Hartman . | |
| 5,330,056 | 7/1994 | De La Rocha | 206/581 |
| 5,366,087 | 11/1994 | Bane | 206/459.5 |
| 5,443,202 | 8/1995 | Jergensen-Beck et al. | 229/146 |
| 5,549,200 | 8/1996 | Cowan et al. . | |

*Primary Examiner*—Paul T. Sewell
*Assistant Examiner*—Nhan T. Lam
*Attorney, Agent, or Firm*—Milton L. Honig

[57] ABSTRACT

A reclosable dispenser is provided which includes an outer case having a cap hingedly attached to a rear wall of the case. A tray is fitted within and slidably removable from a pocket of the case. The tray can contain a plurality of swabs. An open face of the tray is juxtaposed against a front wall of the outer case. The reclosable dispenser can serve as a travel case carrying relatively small amounts of the swabs, laid within the tray, but protected by a relatively thick walled outer case.

16 Claims, 3 Drawing Sheets

SWAB DISPENSER

BACKGROUND OF THE INVENTION

1. Field of the Invention

The invention concerns a reclosable package for dispensing elongated rod shaped articles, especially cotton-tipped swabs. In particular, the dispenser is intended as a travel size package for swabs.

2. The Related Art

Merchandising of certain rod shaped articles, such as cotton-tipped swabs, requires a dispenser for holding a group of these articles in oriented fashion. Single articles must be dispensable from a predetermined dispensing position while a second of the articles of the group is automatically brought into the vacated position. When the article is a cotton-tipped swab, it is important that the article be kept clean. The dispenser must minimize the risk of contamination from dust and dirt. Particularly important is that the dispensing of the product be facile while at the same time minimizing exposure of the remaining swabs to contaminates.

A variety of packaging systems for these purposes have been described in the literature. U.S. Pat. No. 5,147,035 (Hartman) discloses a thermoformed blister of flexible plastic material sealed to a backing card. The package includes a cover and an egress opening. A hinge is provided for the cover which rotatably attaches to the thermoformed blister.

U.S. Pat. No. 3,261,501 (Capucio) discloses a dispenser for rod-shaped articles such as cotton-tipped swabs. The package is designed so that dispensing may be effected without contacting the ends of the articles. When it is desired to dispense the product, passage through a normally closed opening is achieved by using the thumb to engage the article's center portion via a cut-out section.

U.S. Pat. No. 4,989,730 (Lemoine) reports a cotton swab shipping container and dispenser. A removable "T" shaped panel is provided for converting from a shipping container to a dispenser function.

U.S. Pat. No. 5,549,200 (Cowan et al.) provides another solution to delivery and protection of swabs. A blister pack with totally peelable top face is placed within a clear, hard plastic outer case with movable lid. When empty, the blister pack is replaced with a refill. The outer box is retained for reuse. Although a significant advance, the outer box is expensive and heavy. This system is best utilized in institutions rather than in the low volume usage of individual consumers. Better dispensing systems are necessary, especially for the travel size market.

Accordingly, it is an object of the present invention to provide a reclosable dispenser for use with many types of dry goods, but especially cotton swabs, which is relatively inexpensive to manufacture.

Another object of the present invention is to provide a reclosable dispenser for dry goods, especially cotton swabs, which can be proportioned for travel.

Still another object of the present invention is to provide a reclosable dispenser for dry goods, especially cotton swabs, which is amenable to facile filling and alignment of the individual rod shaped articles or swabs in an ordered side-by-side arrangement.

Yet another object of the present invention is to provide a swab dispenser with a relatively sturdy outer housing whose interior can readily be accessed to retrieve one or more swabs in an orderly dispensing arrangement.

These and other objects of the present invention will become more apparent through consideration of the following summary and detailed discussion.

SUMMARY OF THE INVENTION

A reclosable dispenser is provided which includes:

(i) an outer case having parallel front and rear walls, parallel left and right sidewalls orthogonally joining front and rear walls, a bottom wall, an open mouth opposite the bottom wall, the walls and mouth defining a pocket, and a cap hingedly attached to the rear wall; and (ii) a tray fitted within and slidably removable from the pocket, the tray having a floor panel surrounded by parallel upper and lower panels, parallel left and right side panels orthogonally joining upper and lower panels, and a hollow receptacle area being formed by a combination of the panels, the floor panel of the tray being juxtaposed against the rear wall of the outer case and the hollow receptacle area being juxtaposed against the front wall of the outer case.

The cap in a closed position will have its left and right cap walls partially overlapping with the respective left and right walls of the case. Each of the cap walls will further include an inwardly projecting nib engageable into a recess on respective left and right walls of the case. Alternatively, the cap walls may feature the recess while respective left and right walls of the case may have outwardly projecting nibs to engage the respective recess on the adjacent cap wall. By the term "recess" is meant either an aperture fully traversing the wall or merely an indentation.

Advantageously the rear wall is longer in height than the front wall of the outer case. This relative differential height allows the upper panel and a portion of the hollow receptacle of the tray to protrude upwardly through the pocket mouth and above the front wall of the outer case. Only a portion of the tray contents, e.g. cotton swabs, are thereby exposed. Contamination or accidental spillage of the tray contents is avoided.

A further optional feature has the upper panel being perforated at least partially along an edge common with an edge of the floor panel. Further, the upper panel can include a tab portion having an edge common with the edge of the floor panel but not being perforated. When the dispenser is first opened, the upper panel, with the exception of the tab, may be torn away along the perforation lines. By so doing, greater access is achieved to the contents of the tray.

Unlike the larger traditional plastic wrap around swab products, the dispenser of this invention is of a relatively small size suitable for travel. All walls of the outer case are formed of a relatively sturdy plastic having wall thicknesses of at least 0.01 inches, preferably greater than about 0.03 up to 0.3 inches, and optimally about 0.045 inches. Polypropylene is the preferred plastic. The relatively rigid outer case protects a relatively crushable tray which is formed of cellulosic material such as paperboard. Generally walls of the outer case will be more than about twice as thick as that of panels forming the tray.

A still further feature of the dispenser according to the present invention is that of a tamper evident seal. Advantageously the seal will be an adhesive strip, ordinarily being a component of a label attached across a front wall of the outer case. The seal is placed across an interface of the cap with the front wall. Preferably the tamper evident seal is a perforated peel-off strip.

Generally the tray in travel size will contain from about 20 to about 50, preferably about 30 swabs. The swabs are usually elongate rods with a covering of cotton material at opposite ends. Efficiency of packing requires that the swabs be aligned parallel to one another within the tray, their length being parallel to the upper and lower panels thereof.

A paperboard blank for the tray is also provided according to the present invention. The blank includes:

an elongate central floor panel with upper, lower, right and left edges and at least two separate flap lines cut into the central floor panel;

a left panel attached along the left edge of the central panel and forming a crease line therewith, the left panel being divided into first and second areas by a further crease line;

a right panel attached along the right edge of the central floor panel forming a crease line therewith, the right panel being divided into first and second areas by a further crease line; and an upper and lower panel attached along the respective upper and lower edges to the central floor panel forming respective crease lines with the edges, each of the upper and lower panels having left and right wing flaps connected along crease lines to opposite ends of the respective upper and lower panels, the upper edge forming crease line being at least partially perforated.

BRIEF DESCRIPTION OF THE DRAWINGS

The objects, features and advantages of the present invention will become more apparent from the following detailed description taken in conjunction with the accompanying drawing showing a preferred embodiment in which.

DETAILED DESCRIPTION OF THE INVENTION

Figure 1:
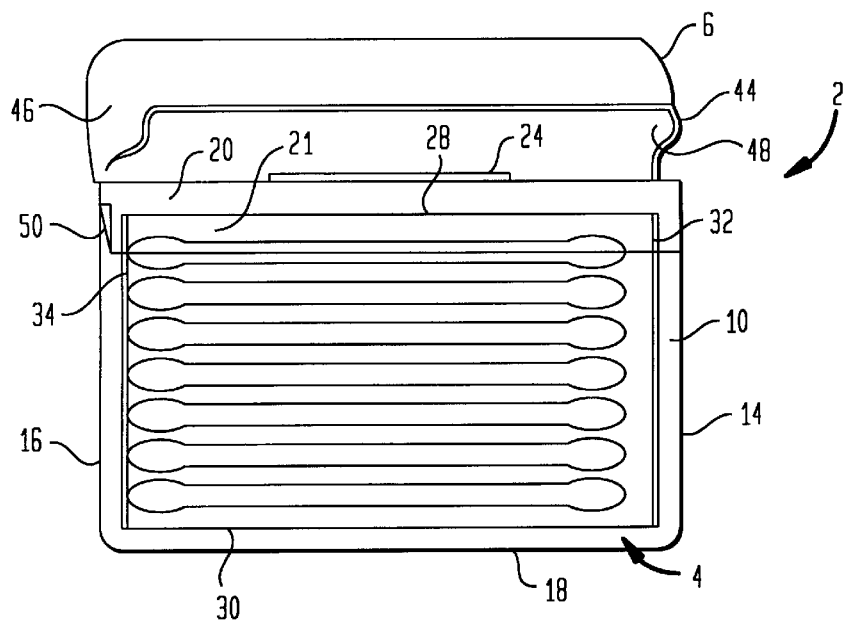
FIG. 1 is a perspective view of the dispenser with the cap in an open position showing the outer case and swab filled inner tray.
Figure 2:
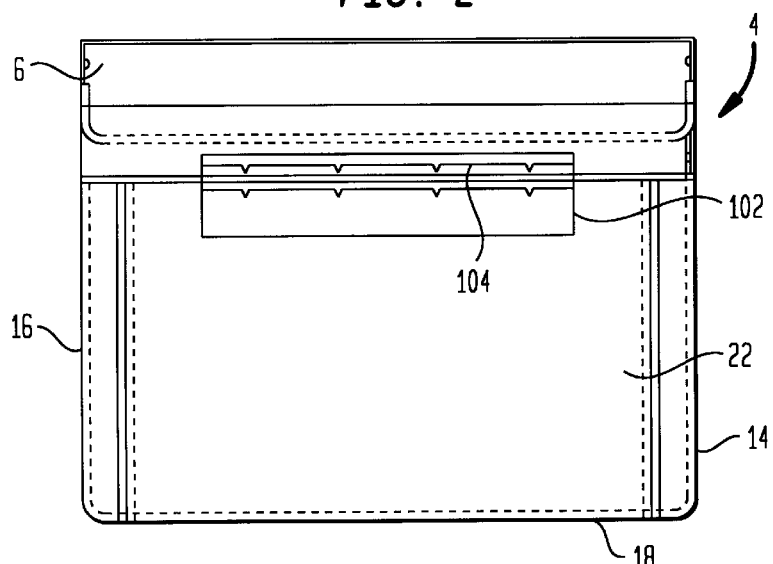
FIG. 2 is a front elevational view of the outer case in a transparent walled embodiment, the tray with swabs being absent.
Figure 3:
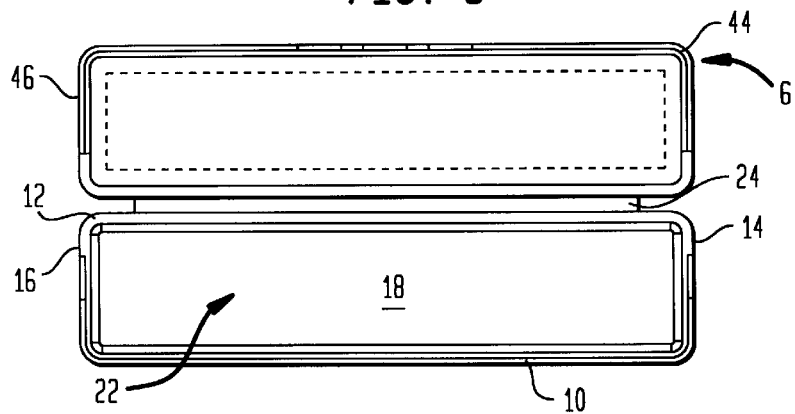
FIG. 3 is a top plan view of FIG. 2 with the cap in its fully opened position.
Figure 4:
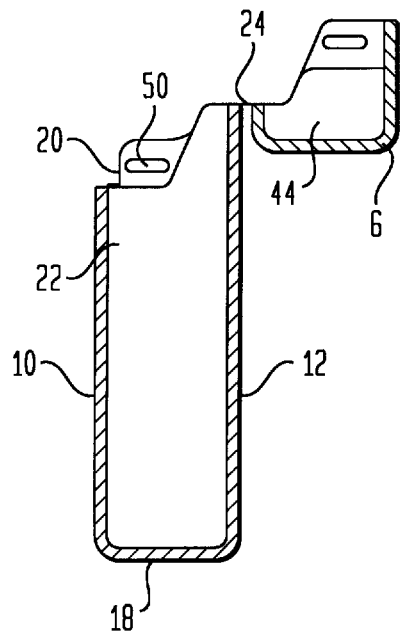
FIG. 4 is a side view of the outer case according to FIG. 2.
Figure 5:
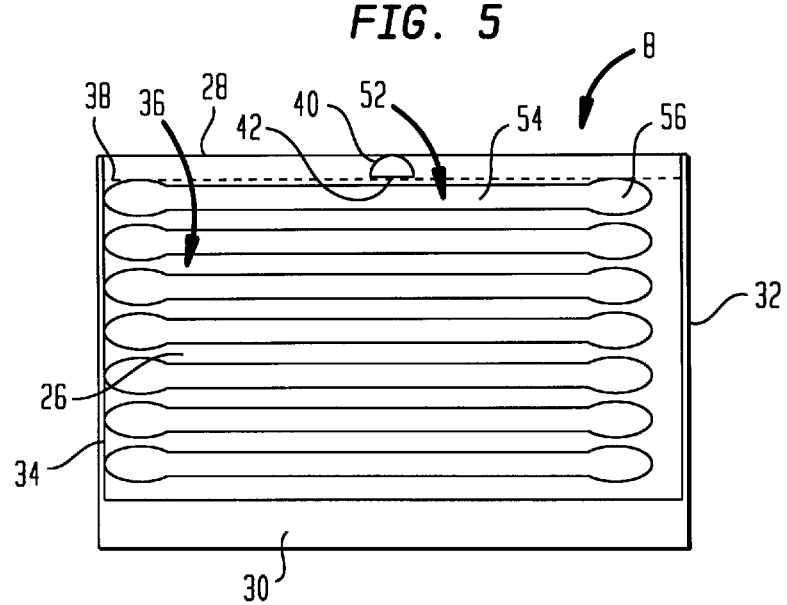
FIG. 5 is a plan perspective view of the tray filled with swabs but outside its outer case.

FIG. 1 illustrates the preferred embodiment of a reclosable dispenser 2 according to the present invention. Dispenser 2 includes an outer case 4 fitted with a cap 6, and a tray 8. The outer case is formed from parallel front and rear walls 10, 12, parallel left and right sidewalls 14, 16, a bottom wall 18 and an open mouth 20 opposite the bottom wall. The left and side right walls orthogonally join front and rear walls. In combination the walls and mouth define a pocket 22. Cap 6 is hingedly attached to the rear wall 12. FIGS. 1, 3 and 4 illustrate the cap in its open position. FIG. 2 illustrates the cap in a closed position. A living hinge 24 is the preferred mechanism by which the cap can pivot from its closed to open position.

Tray 8 is fitted within and slidably removable from the pocket. The tray is formed from a floor panel 26 surrounded by parallel upper and lower panels 28, 30, parallel left and right side panels 32 and 34. The left and right side panels orthogonally join the upper and lower panels. Together the combination of panels define a hollow receptacle area 36. Rear wall 12 of the outer case is juxtaposed against the floor panel 26 of the tray. Concurrently an open face 21 of the tray is juxtaposed against the front wall 10 of the outer case.

In the preferred embodiment as best illustrated in FIGS. 1 and 4, the rear wall 12 is longer in height than the front wall 10 of the outer case. The arrangement allows the upper panel 28 and a portion of the hollow receptacle 36 of the tray to protrude upwards through the mouth 20 and above the front wall of the outer case. Easy access is therefore available to contents of the tray. Nevertheless the full contents of the tray are not exposed to contamination from outside the reclosable dispenser.

Another feature of the preferred embodiment, although it is an optional one, is a tear-away portion of the upper panel. Access to the tray contents thereby becomes even more available. Specifically, the upper panel is perforated at least partially along an edge 38 common with an edge of the floor panel. Additionally, the upper panel includes a tab portion 40 having an edge 42 common with the edge of the floor. Edge 42 is creased but unperforated. When the upper panel is torn away along its perforated edge 38, tab portion 40 remains intact to serve as a pull mechanism to lift the tray thereby exposing further parts of the receptacle area 36. Ordinarily the tray is formed of a cellulosic material such as paperboard.

Cap 6 in a closed position will have its left and right cap walls 44, 46 partially overlapping with the respective left and right sidewalls 14, 16 of the outer case. As best illustrated in FIG. 1, the left and right cap walls each include an inwardly projecting nib 48. The nibs are engageable into a respective recess 50 on respective left and right sidewalls 14, 16 of the outer case. In an alternative embodiment the cap in a closed position can have the left and right cap walls partially overlapping with the respective left and right sidewalls of the outer case. Alternatively each of these left and right sidewalls can include an outwardly projecting nib engageable into a recess on the respective left and right cap walls.

The reclosable dispenser of the present invention is primarily intended as a swab delivery product. Swabs 52 each have an elongate rod 54 with a pair of opposite ends fitted with a soft covering 56 such as cotton. When sized for travel, tray 8 can hold in parallel aligned arrangement anywhere from 20 to 50 swabs, but usually about 30 swabs.

Figure 6:
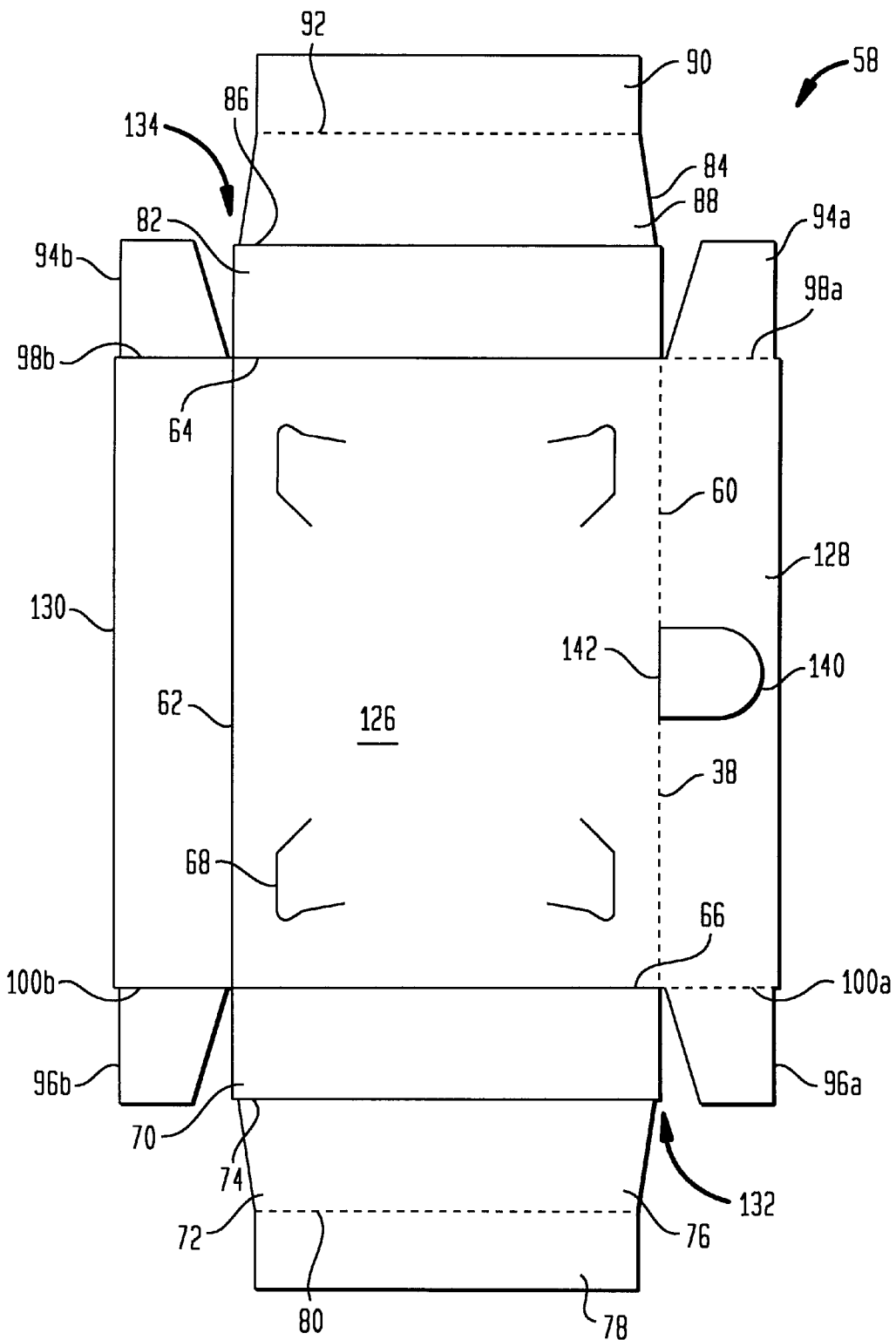
FIG. 6 is a layout of an unassembled tray paperboard blank.

Another aspect of the present invention is that of a paperboard blank. The blank is best illustrated in FIG. 6. Blank 58 consists of an elongate central floor panel 126 having upper 60, lower 62, right 64 and left 66 edges and four separate flap lines 68 cut into the central floor panel. A left panel 132 is attached along the left edge 66, the latter forming a crease line between left and floor panels. Further, the left panel 132 is divided between a first and second area 70, 72 by a left side crease line 74. Second area 72 is further divided into an upper left side segment 76 and a lower left side segment 78, these segments being separated along a left perforated crease line 80.

An arrangement similar to that of the left side panel is found with the right side panel 134. This panel is attached to the right edge of the floor panel forming a right crease line therebetween. The right side panel is further separated into a first and second area 82, 84 by a right side crease line 86. Further, the second area 84 is divided into an upper right side segment 88 and a lower right side segment 90, the segments being separated by a perforation line 92 running parallel to the right side crease line 86.

An upper and lower panel 128, 130 are attached along respective upper and lower edges 60, 62 of the central floor panel, each of these edges forming crease lines. Each of the upper and lower panels are provided with left and right wing flaps 94a, 94b, 96a, 96b, respectively, along upper and lower left and right crease lines 98a, 98b, 100a, 100b, respectively, to opposite ends of the respective upper and lower panels. Upper left and right crease lines 98a, 100a are perforated. Also perforated is the upper edge 60 but only to the borders of a tab edge 142 by which a tab 140 remains attached to the central floor panel after tear-away of wall perforated segments of the upper panel 128.

In another aspect of the invention, a tamper evident seal 102 is placed across an interface of the cap and the front wall of the outer case. The seal has break-away perforation lines 104.

It is to be understood that the invention in its broader aspects is not limited to the specific elements shown and described, but also includes within the scope of the accompanying claims any departures made from such elements which do not sacrifice its chief advantages.

What is claimed is:

1. A reclosable dispenser comprising:
   (i) an outer case having parallel front and rear walls, parallel left and right sidewalls orthogonally joining front and rear walls, a bottom wall, an open mouth opposite the bottom wall, the walls and mouth defining a pocket, and a cap hingedly attached to the rear wall; and
   (ii) a tray fitted within and slidably removable from the pocket, the tray having a floor panel surrounded by parallel upper and lower panels, parallel left and right side panels orthogonally joining upper and lower panels, and a hollow receptacle area with an open mouth opposite the floor panel, the hollow receptacle area being formed by a combination of the panels, the floor panel of the tray being juxtaposed against the rear wall of the outer case, the open mouth of the hollow receptacle area being juxtaposed against the front wall of the outer case, and the upper panel being perforated at least partially along an edge common with an edge of the floor panel.

2. A swab product comprising:
   (a) a plurality of swabs, each swab being an elongate rod with a pair of opposite ends fitted with a soft covering material; and
   (b) a reclosable dispenser for containing the swabs comprising:
      (i) an outer case having parallel front and rear walls, parallel left and right sidewalls orthogonally joining front and rear walls, a bottom wall, an open mouth opposite the bottom wall, the walls and mouth defining a pocket, and a cap hingedly attached to the rear wall; and
      (ii) a tray fitted within and slidably removable from the pocket, the tray having a floor panel surrounded by parallel upper and lower panels, parallel left and right side panels orthogonally joining upper and lower panels, and a hollow receptacle area with an open mouth opposite the floor panel, the hollow receptacle area being formed by a combination of the panels, the floor panel of the tray being juxtaposed against the rear wall of the outer case, and the mouth of the hollow receptacle area being juxtaposed against the front wall of the outer case.

3. The product according to claim 2 wherein the cap in a closed position has left and right cap walls partially overlapping with the respective left and right walls of the outer case, each of the cap walls further comprising an inwardly projecting nib engageable into a recess on the respective left and right sidewalls of the case.

4. The product according to claim 2 wherein the cap in a closed position has left and right cap walls partially overlapping with the respective left and right sidewalls of the outer case, each of the left and right sidewalls of the case further comprising an outwardly projecting nib engageable into a recess on the respective left and right cap walls.

5. The product according to claim 2 wherein the rear wall is longer in height than the front wall of the outer case.

6. The product according to claim 4 wherein the upper panel and a portion of the hollow receptacle of the tray protrudes upwards through the pocket mouth and above the front wall of the outer case.

7. The product according to claim 2 wherein the upper panel is perforated at least partially along an edge common with an edge of the floor panel.

8. The product according to claim 6 wherein the upper panel includes a tab portion having an edge common with an edge of the floor panel but being unperforated.

9. The product according to claim 2 wherein the front, rear and side walls of the outer case are formed of a plastic having a thickness of at least 0.01 to 0.3 inches.

10. The product according to claim 9 wherein thickness is greater than about 0.03 inches.

11. The product according to claim 9 wherein the plastic is polypropylene.

12. The product according to claim 9 wherein the tray is formed of a cellulosic material.

13. The product according to claim 2 further comprising a tamper evident seal across an interface of the cap and the front wall.

14. The product according to claim 2 wherein the covering material is cotton.

15. The product according to claim 2 wherein the plurality of swabs range from about 20 to about 50 in number.

16. The product according to claim 15 wherein the number of swabs is about 30.

* * * * *

UNITED STATES PATENT AND TRADEMARK OFFICE
CERTIFICATE OF CORRECTION

PATENT NO. : 5,938,026
DATED : August 17, 1999
INVENTOR(S) : Thorn

It is certified that error appears in the above-indentified patent and that said Letters Patent is hereby corrected as shown below:

On the title page, item [73] Assignee "Chesebrough-Pond's USA Co.,"

to read -- Chesebrough-Pond's USA Co., Division of Conopco, Inc. --

Signed and Sealed this

Eighth Day of February, 2000

*Attest:*

Q. TODD DICKINSON

*Attesting Officer*    Commissioner of Patents and Trademarks